US012708396B2

(12) United States Patent
Maul et al.

(10) Patent No.: US 12,708,396 B2
(45) Date of Patent: Aug. 18, 2026

(54) INTERVERTEBRAL-PREPARATION TOOL

(71) Applicant: Richard Wolf GmbH, Knittlingen (DE)

(72) Inventors: Silas Maul, Pforzheim (DE); Sebastian Frey, Waghäusel (DE)

(73) Assignee: RICHARD WOLF GMBH, Knittlingen (DE)

( * ) Notice: Subject to any disclaimer, the term of this patent is extended or adjusted under 35 U.S.C. 154(b) by 239 days.

(21) Appl. No.: 18/564,172

(22) PCT Filed: May 25, 2022

(86) PCT No.: PCT/DE2022/200104

§ 371 (c)(1),
(2) Date: Nov. 27, 2023

(87) PCT Pub. No.: WO2022/247998

PCT Pub. Date: Dec. 1, 2022

(65) Prior Publication Data

US 2024/0245418 A1 Jul. 25, 2024

(30) Foreign Application Priority Data

May 28, 2021 (DE) ..................... 10 2021 205 450.1

(51) Int. Cl.

| | |
|---|---|
| ***A61B 17/56*** | (2006.01) |
| ***A61B 17/32*** | (2006.01) |
| *A61B 17/00* | (2006.01) |

(52) U.S. Cl.
CPC .... *A61B 17/32* (2013.01); *A61B 2017/00367* (2013.01); *A61B 2017/320004* (2013.01)

(58) Field of Classification Search
None
See application file for complete search history.

(56) References Cited

U.S. PATENT DOCUMENTS

| | | | |
|---|---|---|---|
| 6,224,604 | B1 | 5/2001 | Suddaby |
| 2019/0038304 | A1 | 2/2019 | Abbasi |

FOREIGN PATENT DOCUMENTS

| | | | |
|---|---|---|---|
| DE | 102012109459 A1 | 4/2014 | |
| WO | 2008035849 A1 | 3/2008 | |

*Primary Examiner* — Jon Eric C Morales
(74) *Attorney, Agent, or Firm* — McGlew and Tuttle, P.C.

(57) ABSTRACT

An intervertebral preparation tool, i.e. a material-removing tool for intervertebral preparation, includes a cutting head (2) which includes at least one movable blade (8) which is held by at least three pivotable levers. The levers (14, 16, 18) are each configured in a rigid manner. A first (14) and a second (16) lever are each articulated at a first articulation point (20) on the blade (8) and at a distanced second articulation point (22) on a carrier element (10) of the cutting head (2), a third lever (18) is articulated at a first articulation point (20) on the blade (8) and at a distanced second articulation point (24) on an actuation rod (26) which is displaceable relative to the carrier element (10). The articulation points (20, 22, 24) are configured as pivot joints with pivot axes which are parallel to one another.

20 Claims, 5 Drawing Sheets

X
26
10
24
18
20
20
16
22
8
12
14

X
26
6
24
18
20
8
2
16
22
14
12

2
X
10
26
18'
24
24
18'
20
20
16'
20
20
16'
8
8
22
22
20
20
14'
14'
22
22
12 x
38
36
26
13
11
9
7
5
15
32

4
34
40
38
36
VIII
26
28
6
x
32
30

INTERVERTEBRAL-PREPARATION TOOL

CROSS REFERENCE TO RELATED APPLICATIONS

This application is a United States National Phase Application of International Application PCT/DE2022/200104, filed May 25, 2022, and claims the benefit of priority under 35 U.S.C. § 119 of German Application 10 2021 205 450.1, filed May 28, 2021, the entire contents of which are incorporated herein by reference.

TECHNICAL FIELD

The invention relates to an intervertebral preparation tool, i.e. a material-removing tool for intervertebral preparation, a so-called paddle shaver.

BACKGROUND

So-called paddle shavers are known for intervertebral preparation, i.e. for the material-removal of the intervertebral disc between the vertebrae before the insertion of an implant. For example, WO 2008/035849 A1 discloses such an instrument which at its distal end comprises a cutting head with two blades. The blades are directed diametrically opposite to the longitudinal axis of the cutting head and are movable via an actuating rod. For this, the blades are each articulated via two levers and are pressed outwards by a spring element. The two levers permit a tilting of the blades to the longitudinal axis of the instrument. Such a tilting is undesirable in the individual case.

SUMMARY

Against this background, it is an object of the invention to provide an improved abrasive tool for the preparation of intervertebral, i.e. a paddle shaver which ensures a defined guidance of the material-removing blades.

This object is achieved by an intervertebral preparation tool, i.e. a material-removing tool for intervertebral preparation with features according to the invention. Preferred embodiments result from this disclosure, including the subsequent description as well as the attached figures.

The intervertebral preparation tool according to the invention is configured for application as a material-removing tool for intervertebral preparation, i.e. a so-called paddle shaver and comprises a cutting head with at least one movable blade. In particular, the blade is movable, in order after the introduction into the intervertebral space, i.e. between two vertebrae, to be able to move it into a position which is radially distanced with respect to the longitudinal axis, in order to be able to remove intervertebral disc material in the complete intervertebral region. The at least one movable blade is held by at least three pivotable levers. I.e. the pivotable levers connect the blade to the cutting head or to the carrier structure of the cutting head and create the desired movability of the blade. The levers themselves are configured in a rigid manner. A first and a second lever are each articulated, i.e. pivotably connected at a first articulation point on the blade and at a distanced second articulation point on a carrier element or a carrier structure of the cutting head. The first and the second articulation point lie on the levers preferably at their opposite ends. A third lever is articulated, i.e. pivotably connected at a first articulation point on the blade and at a distanced second articulation point on an actuation rod. This actuation rod is displaceable relative to the carrier element. The first and the second articulation point on the third lever likewise preferably lie at the opposite ends of this lever. By way of displacing the actuation rod, the third lever can herewith be moved relative to the carrier element, by which means a moving of the blade or spreading of the instrument in the region of the cutting head is possible for widening the diameter. For this, the articulation points are configured as pivot joints whose pivot axes extend parallel to one another. Thus, in particular, a pivoting of the levers is possible and this effects a movement of the cutting blade in the radial direction with respect to the longitudinal axis of the instrument or of the cutting head, in order to widen the diameter. The arrangement of three levers which carry the blade on the cutting head has the advantage that a tilting of the blade in a manner such that a change of the angular position to the longitudinal axis of the cutting head which extends from the proximal to the distal end is no longer possible and thus the blade is held in a defined angular position. The angular position relative to the longitudinal axis can be constant or change in a defined manner with the movement of the third lever. An undefined tilting of the blade however is prevented by the use of three levers.

Preferably, the material-removal tool comprises a second blade. This blade can be rigid. Preferably, the cutting head however comprises two movable blades, wherein these two blades are each held by three pivotable levers as have been described beforehand. I.e. each of the two blades is held on the cutting head via three rigidly configured levers, wherein a first and a second lever are each articulated at an articulation point on the associated blade and at a distanced second articulation point on the carrier element. Herein, the first and the second levers of the two blades can be articulated on the carrier element at separate second articulation points. However, it would also be conceivable for both first levers to be pivotably articulated at a common second articulation point and/or for both second levers to be pivotably articulated at a common second articulation point, on the carrier element. Furthermore, each of the blades comprises a third lever which is articulated at a first articulation point on the associated blade and at a distanced second articulation point on the actuation rod which can be displaced relative to the carrier element. The articulation points are configured as pivot joints with pivot axes which are parallel to one another, wherein in particular the pivot axes of the articulation points of both blades also run parallel to one another. A common second articulation point on the actuation rod could also be provided for both third levers. Moreover, the third levers on a blade could be articulated to a second lever each at a common first articulation point.

The at least one blade or blades are expediently configured such that their longitudinal edges, i.e. their long edges which preferably extend essentially in the longitudinal direction of the instrument are configured in a cutting manner or act as cutting edges. The blades therefore act in a cutting or material-removing manner in the circumferential direction with respect to the longitudinal axis of the instrument or tool. The tool can thus be used in a manner such that a cutting or material-removal can be effected by way of a movement transverse to the instrument longitudinal axis and/or rotation about the instrument longitudinal axis.

The two third levers preferably form a toggle lever mechanism which by way of displacing the actuation rod presses the two blades apart or in the reverse direction pulls them together, so that the instrument in the region of the cutting head can be widened or made smaller in the direction of the diameter, wherein the diameter is defined by the radial distance of the blades. By way of the arrangement of the three levers on each blade, herein the angular position of the two blades to one another is fixedly set. I.e. the two blades cannot pivot to one another in an undefined manner or change their angular position to one another.

Preferably, the two blades are arranged at opposite sides of the longitudinal axis of the cutting head. The longitudinal axis of the cutting head is herein the axis which extends from the proximal to the distal end. The blades are further preferably arranged at diametrically opposite sides with respect to the longitudinal axis, so that the blades or the distance of the outer sides of the blades to one another defines the diameter of the cutting head. By way of moving one blade or both blades in a direction transverse to the longitudinal axis, in particular in the radial direction, the diameter or the distance of the blades to one another can be changed. Further preferably, the two blades are arranged symmetrically to one another, i.e. in particular in a mirror-imaged manner with respect to the longitudinal axis or a plane, in which the longitudinal axis is situated. In particular, if both blades are movable, the blades are preferably moved symmetrically to one another away from the longitudinal axis or towards the longitudinal axis which as described above can be realized via the third levers which then form a type of toggle lever joint.

The second articulation points of the three levers for holding a blade, i.e. a single blade are preferably distanced to one another in a direction transverse to the pivot axes. If two blades are provided, then further preferably the second articulation points of the three levers of both blades are distanced to one another in a direction transverse to the pivot axes. The direction transverse to the pivot axes is preferably a direction parallel to the longitudinal axis of the cutting head. The pivot axes preferably extend transversely, in particular at right angles to the longitudinal axis of the cutting head. A large stability is achieved by the distanced arrangement of the articulation points. For example, the first and the second lever together with the blade and the carrier element could form a parallelogram structure. A third lever preferably does not extend parallel but at an angle to the other two levers, so that the tilting is prevented and a force transmission in all directions is possible. Preferably, in the state in which the blade is radially extended, at least two levers are not parallel to one another. The radially extended state is a state in which the blade in the radial direction is distanced further from the carrier element or the longitudinal axis of the cutting head than in its idle position. In the idle position, the blade is situated in the position in which it has the smallest distance to the longitudinal axis of the cutting head and preferably bears on the carrier element in a direct manner. In this idle state, all three levers which carry a blade can extend essentially parallel to one another or along an axis, so that as a whole the diameter of the instrument is minimized in this state.

Further preferably, on the cutting head, the first lever forms a distal-side lever and the third lever a proximal-side lever, wherein the second lever is arranged between the first and the third lever. The distal-side lever is that lever which is situated furthest to the distal end of the cutting head, whereas the proximal lever is that lever which is situated furthest to the proximal end. The three levers for each present blade which is articulated via three levers are thus arranged offset to one another in the direction of the longitudinal axis of the cutting head. Herein, the levers are preferably offset so far that that they are located completely behind one another in the longitudinal direction in the folded-together state in which the cutting blade is situated in its idle position and in the position which lies radially innermost. One can therefore achieve a small as possible instrument diameter in the folded-together or retracted state. I.e. in this state, the second articulation point of the first lever preferably lies furthest distally and the first articulation point of the first lever lies further distally than the second articulation point of the second lever. The first articulation point of the second lever in turn lies further distally than the third lever, in particular than the first articulation point of the third lever. Particularly preferably, the second articulation point of the third lever on the actuation rod lies furthest proximally.

According to a further preferred embodiment, on a blade, the first articulation points of the first and second lever and preferably the first articulation points of the first, second and third lever are distanced to one another in a direction transverse to the pivot axes, i.e. preferably parallel to the longitudinal direction of the cutting head. This on the one hand permits a parallelogram structure as has been described above. Independently of this, on the other hand a uniform force transmission between the blade and carrier element can be achieved, which in particular prevents a tilting of the blade. Moreover, this arrangement together with the distances of the second articulation points and corresponding lever lengths permits an idle position, in which the levers lie behind one another in the axial direction in the previously described manner. If two blades are each arranged on the carrier element in a movable manner via three levers, then the articulation points are preferably arranged on both blades in a corresponding manner, preferably in the manner described above symmetrically to the longitudinal axis or to a plane which extends along the longitudinal axis.

The levers and their articulation points are further preferably situated and dimensioned such that by way of pivoting the levers about their second articulation points, the associated blade is movable from a first position which is close to the carrier element into at least one second position which is distanced further from the carrier element. Herein, the position which is close to the carrier element is the previously mentioned idle position. On pivoting, the levers rotate about their second articulation points on the carrier element, so that the distance of the first articulation points on the blade in the radial direction to the longitudinal axis of the carrier element increases and the blades are extended in the radial direction or are moved away from the carrier element and the longitudinal axis.

Preferably, the first and the second lever are articulated such that they pivot in the same rotation direction for moving the connected blade. Preferably, the levers herein pivot such that the first articulation points with the blade apart from the movement in the radial direction simultaneously move distally in the longitudinal direction. This can be effected for example in the manner of a parallelogram guidance and if the levers are configured differently long then herein one can simultaneously succeed in a defined oblique position of the blade being reached, said position deviating from the exact parallelogram guidance.

Further preferably, the third lever is articulated such that for moving the connected blade it pivots in a rotation direction which is opposite to the rotation direction of the first and/or second lever given their simultaneously pivoting. I.e. the third lever for example can move such that the first articulation point of the third lever on the blade pivots in the proximal direction relative to the second articulation point. By way of the movement of the actuation rod however, preferably the second articulation point simultaneously moves in the distal direction, so that as a whole the complete third lever retains its position relative to the carrier element or is moved in the distal direction. By way of the pivoting movement in the opposite direction one succeeds in the third lever extending at an angle to the second lever and preferably to the first and second lever so that all three levers together do not form a parallelogram arrangement and thus a tilting of the blade is prevented. I.e. the second and the third lever preferably extend oppositely at an angle to the radius with respect to the longitudinal axis. If two blades are provided, their third levers as described above are moved via the actuation rod preferably in the manner of a toggle lever joint, so that by way of the axial displacement of the actuation rod the first articulation points of the third levers are pressed radially outwards so that the two blades are moved apart. The blades can accordingly be moved together again in the opposite direction, i.e. back into an idle position bearing on the carrier element.

The first and the second lever which are articulated on a blade, i.e. on the same blade, can have the same length between their first and second articulation points. If simultaneously the distance of the first articulation points from one another and the distance between the second articulation points is the same, then herewith one essentially creates a parallelogram shape or parallelogram arrangement, as has been described beforehand.

Furthermore, it is possible for the second lever and third lever which are articulated onto a blade to have the same length between their first and second articulation points. This has the effect that the second lever and third lever on pivoting define a triangular or trapezoid shape to one another, said shape in particular permitting a force transmission in the distal as well as proximal direction between the blade and the carrier element or actuation rod. This design prevents the tilting of the blade, so that the angular position of the blade relative to the longitudinal axis of the cutting head is prevented from changing in an undefined manner.

In a special embodiment, the first lever and the second lever which are articulated on a blade, i.e. on the same blade, can have different lengths between their first and second articulation points, wherein e.g. the first lever which forms a distal-side lever on the cutting head is configured longer than the second lever. Alternatively, the first lever could also be shorter than the second lever. By way of this once succeeds in the angular position of the blade relative to the longitudinal axis of the cutting head changing simultaneously on moving the blade radially outwards by way of pivoting the third lever. I.e. the blade does not move parallel in the radial direction, but simultaneously pivots by a certain mount given the radial movement. A lordosis angle thus forms, which can be desirable for certain application purposes.

The second and the third lever which are articulated on a blade, i.e. on the same blade, can have different lengths between their first and second articulation points, wherein e.g. the second lever is configured longer than the third lever. Another length for the third lever can have advantages with regard to the function of the third lever for the extending movement or radial movement of the blade. Moreover, it can be advantageous to design the third lever shorter in the case that the first lever is longer, in order to be able to realize a desired lordosis angle, i.e. a conical shape of the cutting head. Conversely, the third lever could be longer in the case e.g. that the first lever is shorter.

Preferably, the cutting head is situated at the distal end of an instrument shank and the actuation rod is displaceably guided on or in this in the longitudinal axis of the instrument shank. Thus, a relative movement between the actuation rod and the instrument shank or a carrier element which is fixedly connected to the instrument shank is realized at the distal end. The second articulation point of the third lever is displaced due to this relative movement, so that this lever then is given an interaction with the first and second lever leads to the associated cutting blade being displaced radially outwards with respect to the longitudinal axis and the cutting head being widened. The widening is preferably achieved by the advance of the actuation rod in the distal direction and the contraction of the cutting head is again achieved by a reversed movement of the actuation rod in the proximal direction.

The cutting head is preferably configured such that when the blade or the blades are in their contacting idle position, it comprises a blunt tip at the distal end, said tip preferably being attached directly to the carrier element or being formed by the carrier element itself. The blunt tip accommodates the forces which occur when the instrument is driven into the intervertebral space. In this state, the blades or the blade are preferably situated behind the blunt tip seen in the longitudinal direction, so that the lever mechanism of the blades is not loaded by the forces with this driving-in. On widening the blades, apart from the radial movement, these can also displace in the distal direction such that they project beyond the blunt tip or the blunt end in the distal direction. This also permits a material-removal in the region of the distal end of the cutting head.

The second articulation points of the three levers which are articulated on a blade, i.e. on the same blade are preferably situated on a straight line which further preferably extends parallel to the displacement direction of the actuation rod, i.e. preferably parallel to the longitudinal axis of the instrument shank or the cutting head. This arrangement encourages the simultaneous pivoting of the three levers in a manner such that the cutting blade is moved radially outwards. In particular, a parallelogram-like structure can hence be created, as has been described above.

According to a further preferred embodiment, the first articulation points of the three levers which are articulated on a blade, i.e. on the same blade, lie on a straight line which extends parallel to or at an angle to the displacement direction of the actuation rod. It is also possible for an angle between this straight line and the displacement direction or longitudinal axis to change during the pivoting-out or widening, in order to create a lordosis angle as has been described previously. In the folded-together idle state, i.e. in the state in which the blade bears on the carrier element, the straight line on which the first articulation points lie preferably extends parallel to the displacement direction or longitudinal axis.

For example, in order to be able to provide a desired lordosis angle, at least one outer side of the blade in at least one position can extend in a manner angled to a longitudinal axis of the cutting head or of the instrument. In this manner, one can also create a constant lordosis angle which is not dependent on the deflection of the levers. The levers can then be configured such that a parallel displacement of the cutting blade to the longitudinal axis is effected in the radial direction and the lordosis angle which is preferably given by the angle of the blade outer side is constant.

The cutting head is preferably arranged at the distal end of an instrument shank, wherein a handle which comprises an actuation device which is coupled to the actuation rod for its displacement is arranged at the proximal end of the instrument shank. I.e. by way of actuation of the actuation device, the actuation rod can be linearly displaced in the desired manner. The actuation device for example can be a spindle drive which comprises a rotary wheel which rotates on a threaded spindle. Herein, the rotary wheel is fixed axially in the handle, so that by way of rotating the actuation wheel the spindle can be advanced and retracted in the longitudinal direction. This linear movement can be transmitted onto the actuation rod. For this, the actuation rod can be fixedly connected to an actuation device such as e.g. the threaded spindle. Preferably, a releasable coupling can be provided. Thus, for example the instrument shank and the actuation rod can be configured in a manner in which they are removable from the handle, in order to be able to design the instrument shank with the cutting head as an article for single use, whereas the handle can be reused. Furthermore, a fixation device for the releasable fixation of the instrument shank to the handle can be provided in the handle. This for example can be a clamping screw.

According to a further preferred embodiment, the actuation device comprises a scale which displays the measure of the widening of the cutting head, i.e. the measure of the radial movement of the blade or the blades. Since the radial displacement of the blade or blades is effected via the deflection of the levers, there is possibly no linear relation between an amount by which the actuation device is moved and the deflection of the blade. This can be taken into account given the design of a scale on the handle and thus the scale can be configured in a non-linear manner and display the amount by which the blades are deflected given the respective position of the actuation device, for example of the linear advance position of the actuation rod.

The invention is hereinafter described in more detail by way of attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
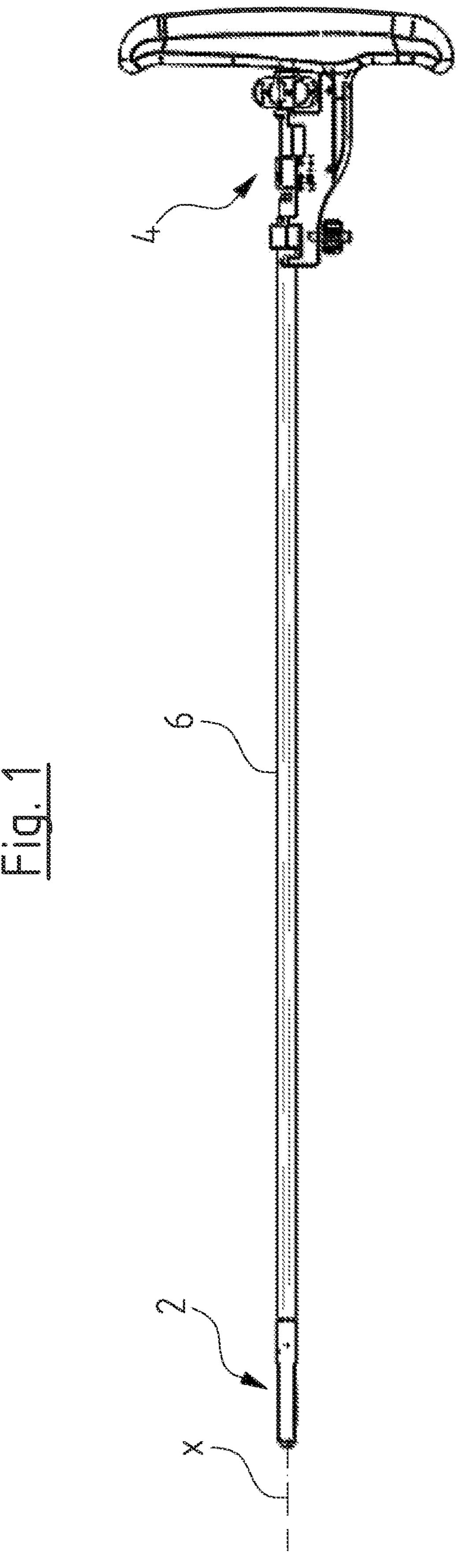
FIG. 1 is a total view of the material-removal tool for the intervertebral preparation according to the invention.
Figure 3:
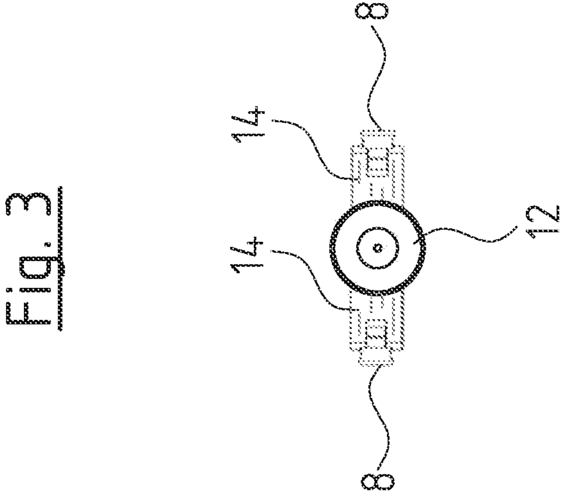
FIG. 3 is a plan view of the cutting head according to FIG. 2.
Figure 2:
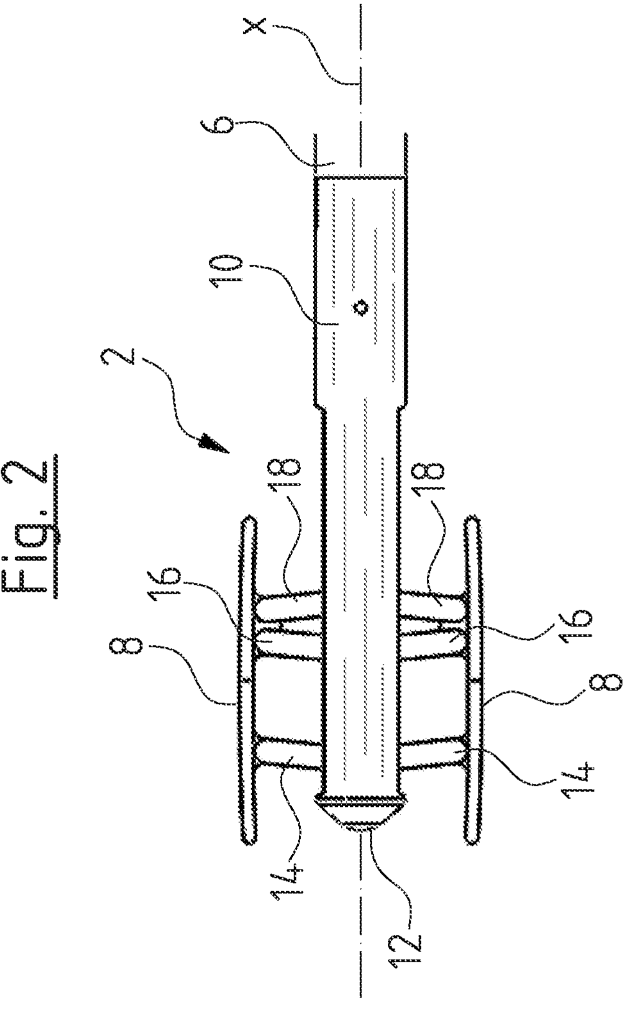
FIG. 2 is a detailed view of the cutting head of the material-removing tool according to FIG. 1 in the widened state.

Referring to the drawings, FIG. 1 in a lateral view shows the material-removing tool as a total instrument. The total instrument consists essentially of three parts, a cutting head 2 at the distal end, a handle 4 at the proximal end and an instrument shank 6 which extends in the distal direction from the handle 4 to the cutting head 2.

The cutting head 2 in this embodiment example is fixedly arranged on the distal end of the instrument shank. The instrument shank as is described hereinafter is releasably connected to the handle 4. The instrument shank and the cutting head 2 are configured for example as single-use instrument, whereas the handle can be used several times, or the handle 4 and the instrument shank 6 can be separated e.g. for cleaning.

The cutting head 2 comprises two blades 8 which are articulated on the carrier element 10 via levers. The carrier element 10 is fastened to the distal end of the instrument shank 6 or can also be configured as one piece with this as a whole or in parts. The distal end of the carrier element 10 is configured as a blunt tip 12 which on insertion or striking of the instrument accommodates the occurring forces.

Each of the blades 8 is connected to the carrier element 10 via three levers, a first lever 14, a second lever 16 and a third lever 18. The first lever is situated distally, the third lever proximally and the second lever 16 therebetween. The arrangement of the two blades 8 with their levers 14, 16 and 18 is mirror-symmetrical to the longitudinal axis X of the instrument or of the cutting head 2 which extends from the proximal to the distal end.

The levers 14, 16 and 18 are articulately connected to the blades 8 each via first articulation points 20 which form pivot axes or are configured as pivot axes. The levers 14, 16, 18 can pivot relative to the blades 8 about the articulation points 20. At their opposite longitudinal end, the first lever 14 and the second lever 16 are each pivotably fastened to the carrier element 10 via a second articulation point 22. The third levers 18 at their ends which are opposite to the first articulation points 20 are each pivotably connected to an actuation rod 26 via a second articulation point 24. The actuation rod extends in the direction of the longitudinal axis X in the inside of the instrument shank 6 and can be displaced forwards and backwards relative to this and relative to the carrier element 10 in the longitudinal direction X. The pivot axes which are defined by the articulation points 20, 22 and 24 extend normally to the longitudinal direction X and thus to the movement direction of the actuation rod 26.

Figure 4:
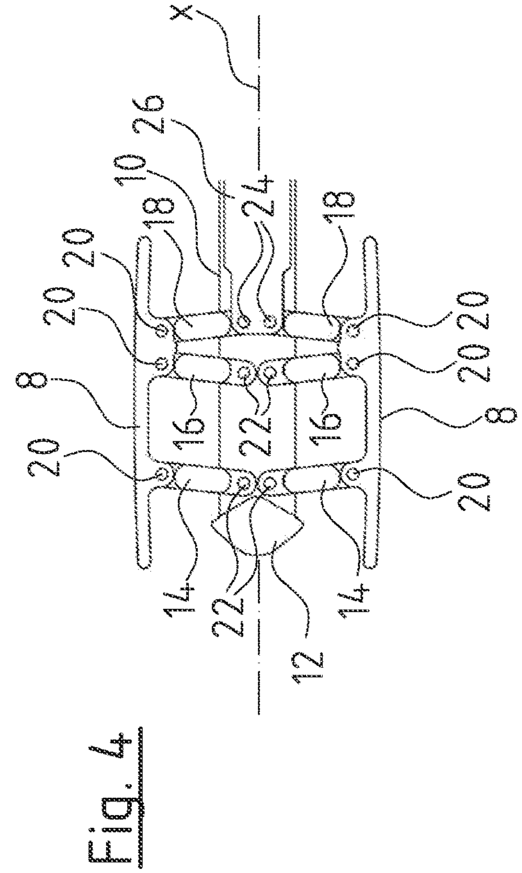
FIG. 4 is a partly sectioned view of the cutting head according to FIG. 2.
Figure 5:
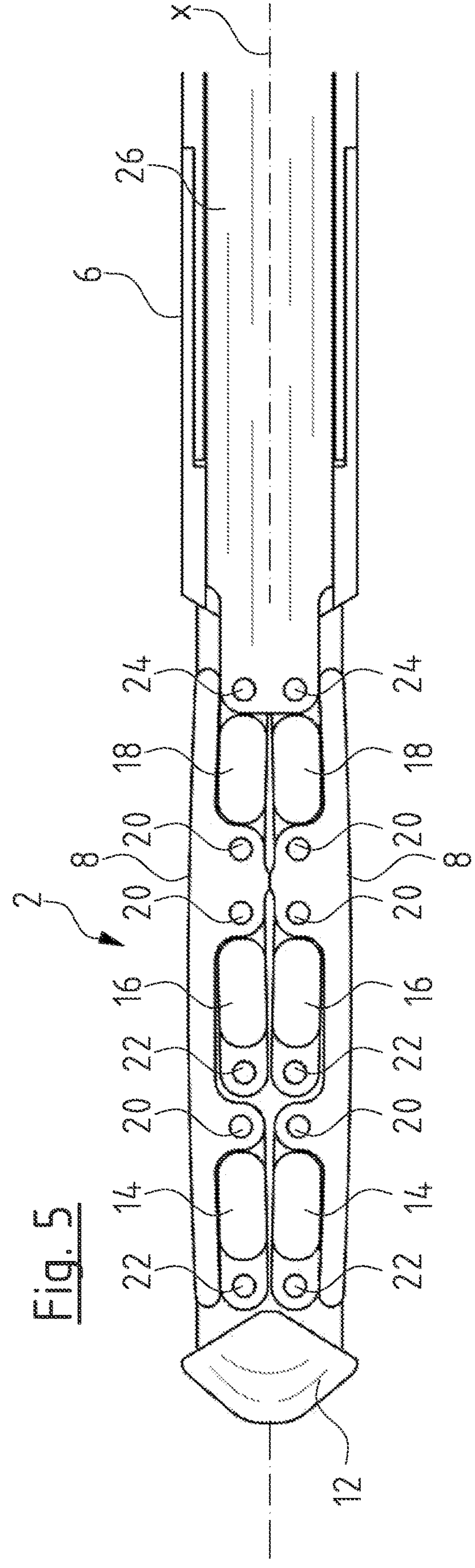
FIG. 5 is a view of the cutting head according to FIG. 4 in the idle state.

In the example which is shown in FIGS. 4 and 5, the first levers 14 and the second levers 16 are equally long and their first articulation points 20 are distanced equally far in the direction of the longitudinal axis X as the second articulation points 22. The first and the second levers 14, 16 with their respectively assigned blade 8 therefore form a parallelogram arrangement. FIG. 4 shows the blades 8 in their extended state, in which they are distanced maximally from the longitudinal axis X in the radial direction, i.e. in this state the cutting head has its largest diameter. FIG. 5 shows the idle state in which the cutting blades 8 essentially bear on the carrier element 10. Herein, the blades 8 lie behind the tip 12 at the proximal side so that the blades 8 are protected by the blunt tip 12 on inserting or striking-in. In the extended state which is shown in FIG. 4, the blades 8 are not only moved in the radial direction but by the parallel pivoting with the levers are also moved distally, so that the distal ends of the blades 8 project beyond the tip 12. The cutting head can therefore act in cutting manner up to its distal end.

In order to move the blades 8 radially outwards out of the idle state which is shown in FIG. 5, the first and second levers 14 and 16 pivot in the same direction about their second articulation points 22 or second pivot axes 22 in a manner such that the first articulation points 20 of the first levers 14 and the second levers 16 move in the arc distally towards the tip 12 and thus move the blades 8 radially outwards and simultaneously distally, wherein the blades 8 extend parallel to the longitudinal axis X in a constant manner. This movement is created by way of the actuation rod 26 being pushed distally. Herein, the second articulation points 24 of the third levers 18 displace distally, by which means the third levers 18 pivot about their second articulation points 24 and hence press the first articulation points 20 via which they are fastened to the blades 8 radially outwards. Herein, the third lever 18 of the two blades 8 together with the actuation rod 26 form a type of toggle lever, concerning which the actuation rod 26 engages centrally on the "toggle". Hence a large force in the radial direction transverse to the longitudinal axis X can be achieved via a comparatively small force in the direction of the longitudinal direction X.

Given their movement, the third levers 18 pivot in the opposite direction to the second levers 16 on the respective blade 8. This has the effect that the third levers 18 do not extend parallel to the second levers 16 but are always directed in an angled manner to these, so that the second lever 16 and the third lever 18 are directed to one another in a V-shaped or trapezoidal manner on each of the blades 8, wherein their first articulation points 20 are situated closer to one another parallel to the longitudinal axis X than the second articulation points 22 and 24. By way of this embodiment one prevents the angular positions of the blades 8 relative to the longitudinal axis X being able to inadvertently change. Whereas the first and second levers 16 and 18 starting from the carrier element 10 extend in the proximal direction obliquely to the longitudinal axis X towards their first articulation points 20, the third levers 18 starting from the actuation rod 26 extend in the distal direction obliquely to the longitudinal axis X towards their first articulation points 20. Depending on how far the actuation rod 26 is advanced in the distal direction, the blades 8 starting from the longitudinal axis X move radially outwards to a different extent. Thus the diameter or the distance of the blades 8 transverse to the longitudinal axis X can be varied and set.

In the idle state which is shown in FIG. 5, the levers 14, 16 and 18 of each of the two blades 8 extend essentially in a line with only very slight angles to the longitudinal axis X. In order to ensure that starting from this idle state the levers pivot given the advance of the actuation rod 26, it is important for the force which is introduced onto the levers 18 via the actuation rod 26 not to extend precisely in the direction of a straight line through the first articulation point 20 and the second articulation point 24 of the third levers 18. I.e. the connection line which forms the middle point of the first articulation point 20 and of the second articulation point 24 extends at an angle to the longitudinal axis X in the idle position which is shown in FIG. 5. The respectively defined longitudinal axes of the first levers 14 and second levers 16 which extend through the middle points of the first articulation points 20 and associated articulation points 22 extend at an acute angle to the longitudinal axis X. In the example which is shown here, all first articulation points 20 on a blade 8 lie on a straight line which runs parallel to the longitudinal axis X. Accordingly, the associated second articulation points 22 and 24 of each of the blades 8 likewise essentially lie on a straight line which extends parallel to the longitudinal axis X. In order to permit the pivoting movement of the third levers 18 opposite to the pivoting movement of the first levers 14 and second levers 16, the third levers 18 are each arranged on the associated blade 8 such that the first articulation point 20 is situated further distally than the associated second articulation point 24. This is the other way around with regard to the first lever 14 and the second lever 16. There the second articulation point 22 lies further distally than the first articulation point 20.

Figure 6:
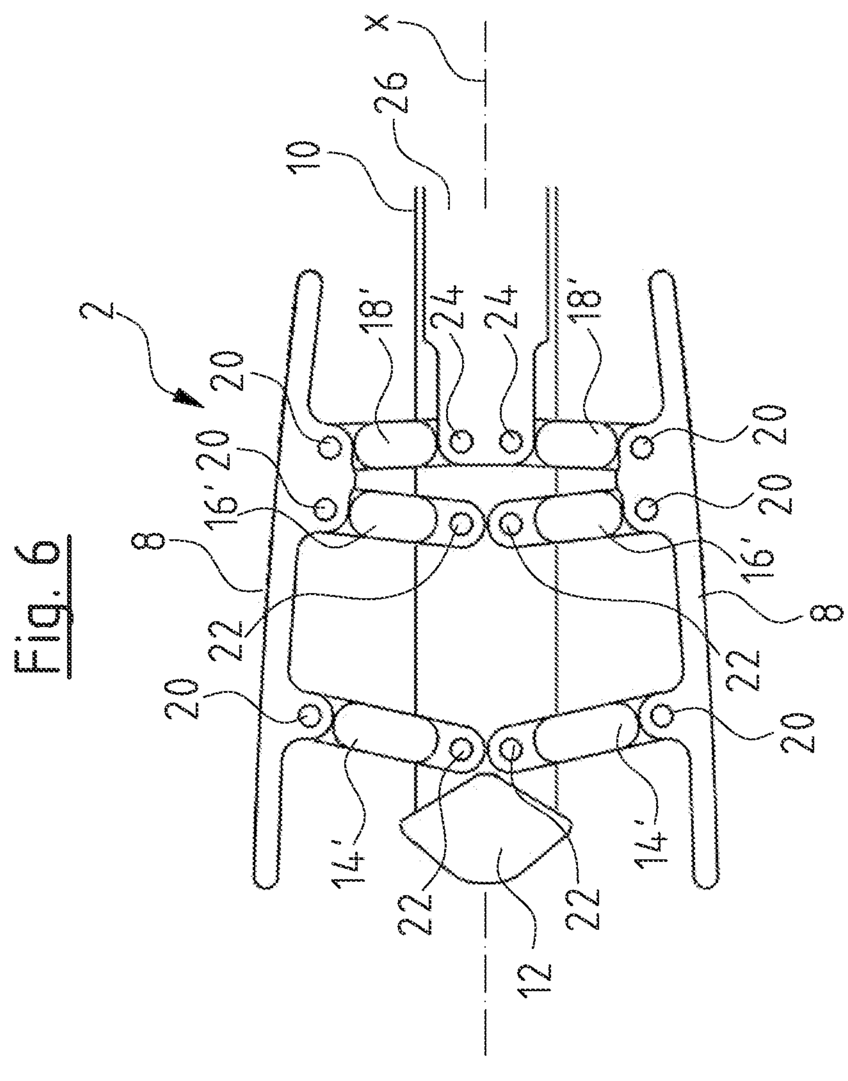
FIG. 6 is an alternative embodiment of a cutting head according to the invention in the widened state.

In the examples which are shown in FIGS. 2 to 5, the outer sides of the blades 8 extend essentially parallel to the longitudinal axis X, i.e. essentially no lordosis angle is provided between the blades 8. A first possibility as to how a lordosis angle could be configured would be to design the outer sides of the blades 8 obliquely to the straight line which runs through the first articulation points 20. A second alternative is shown in FIG. 6. Concerning the embodiment example according to FIG. 6, a lordosis angle is realized by way of the levers 14', 16,' and 18' which articulate the blades 8 to the carrier element 10 not being configured equally long. In the example which is shown here, the first levers 14' between their first articulation points 20 and the articulation points 22 each have a greater length than the second levers 16'. The third levers 18' in turn are configured shorter than the second levers 16'. This has the effect that the first levers 14' and 16' on each of the blades 8 are no longer arranged in an exactly parallel manner and do not form an exact parallelogram structure. On widening, this leads to the blades 8 aligning themselves to the longitudinal axis X in an increasingly angled manner on extending or pivoting blades 8 out of an idle position according to FIG. 5. I.e. here no constant lordosis angle is created, but the lordosis angle essentially increases with the widening or extending of the blades 8 in the radial direction, in the shown example from about 0 degrees to 9 degrees.

Figure 8:
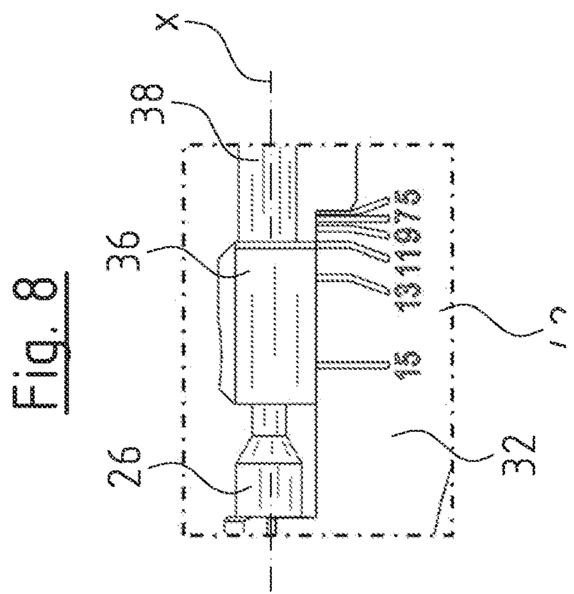
FIG. 8 is an enlarged, the detail VII in FIG. 7.
Figure 7:
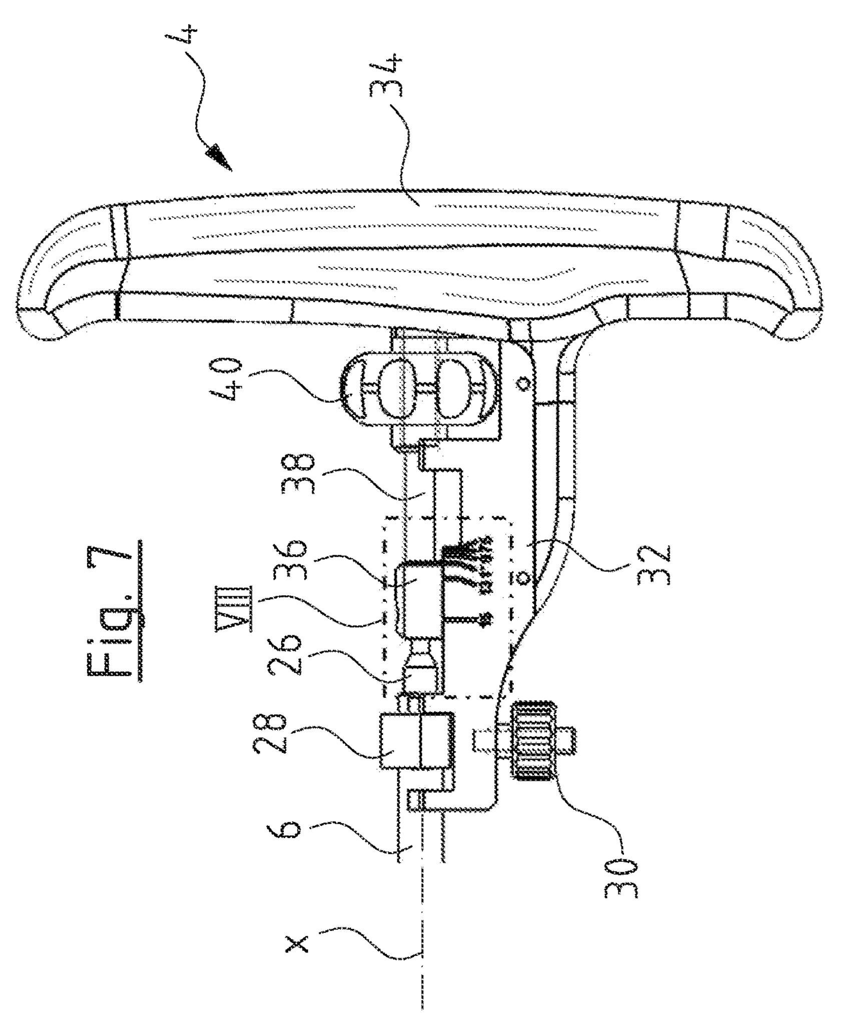
FIG. 7 is a detailed view of the handle.

FIGS. 7 and 8 show a detailed view of the handle 4. The instrument shank 6 or its outer shank is clampingly fixed to the handle 4 via a holding arm 28. For the clamping, the holding arm 28 can be adjusted relative to a grip base 32 via a knurled screw 30, so that the instrument shank 6 can be clamped between the holding arm 28 and the grip base 32. The actuation rod 26 is connected at its proximal end to a slide 36 by way of a positive fit, said slide being slidingly guided on the grip base 32 in the direction of the longitudinal axis X. A threaded rod 38 which extends in the direction of the longitudinal axis X and engages into an actuation device in the form of an adjusting wheel 40 is attached to the slide 36. The adjusting wheel 40 is secured in the grip base 32 in the axial direction, so that on rotation of the adjusting wheel 40 the threaded rod 38 is displaced in its interior in the longitudinal direction X via a threaded engagement. The coupled actuation rod 26 is likewise displaced in the axial direction or the longitudinal direction X via the threaded rod 38, in order to being able to move the blades 8 apart and towards one another in the described manner.

In order to be able to recognize the position of the blades 8 at the handle 4, a scale 42 is formed on the grip base 32, said scale in interaction with the slide 36 displaying the measure of the radial deflection or widening of the blades 8. Since the displacement of the actuation rod 26 is not converted into radial movement of the blades 8 in a linear manner due to the lever mechanism, the scale 42 is not configured in a linear manner. The scale distances increase with an increasing displacement of the slide 36 in the distal direction. The measure of radial widening, i.e. the diameter of the cutting head between the blades 8 can be read off at the handle 4 from the relative position of the slide 36 to the scale 42.

While specific embodiments of the invention have been shown and described in detail to illustrate the application of the principles of the invention, it will be understood that the invention may be embodied otherwise without departing from such principles.

LIST OF REFERENCE NUMERALS

2 cutting head
4 handle
6 instrument shank
8 blades
10 carrier element
12 tip
14, 14' first lever
16, 16' second lever
18, 18' third lever
20 first articulation point
22, 24 second articulation point
26 actuation rod
28 holding arm
30 knurled screw
32 grip base
34 grip piece
36 slide
39 threaded rod
40 adjusting wheel
42 scale
X longitudinal axis

The invention claimed is:

1. An intervertebral preparation tool comprising: a cutting head which comprises a carrier element and at least one movable blade which is held by at least three pivotable levers, wherein the levers each comprise a rigid configuration; and an actuation rod, wherein a first lever and a second lever are each articulated at a first articulation point on the same one blade and at a distanced second articulation point on the carrier element of the cutting head, wherein a third lever is articulated at a first articulation point on the blade and at a distanced second articulation point on the actuation rod which is displaceable relative to the carrier element, and wherein the articulation points are configured as pivot joints with pivot axes which are parallel to one another.

2. An intervertebral preparation tool according to claim 1,
wherein the cutting head comprises two movable blades which are each held by the three pivotable levers,
wherein the levers are each configured rigidly,
wherein a first and a second lever are each articulated at a first articulation point on the associated blade and at a distanced second articulation point on the carrier element,
wherein a third lever is articulated at a first articulation point on the associated blade and at a distanced second articulation point on the actuation rod which is displaceable relative to the carrier element, and
wherein the articulation points are configured as pivot joints with pivot axes which are parallel to one another.

3. An intervertebral preparation tool according to claim 2, wherein the two blades are arranged at opposite sides of a longitudinal axis of the cutting head.

4. An intervertebral preparation tool according to claim 1, wherein the second articulation points of the three levers for holding the blade are distanced to one another in a direction transverse to the pivot axes.

5. An intervertebral preparation tool according to claim 1, wherein on the cutting head the first lever forms a distal-side lever and the third lever a proximal-side lever and the second lever is arranged between the first lever and the third lever.

6. An intervertebral preparation tool according to claim 1, wherein on the blade the first articulation points of the first and the second lever and preferably the first articulation points of the first, the second and the third lever are distanced to one another in a direction transverse to the pivot axes.

7. An intervertebral preparation tool according to claim 1, wherein the levers and their articulation points are situated and dimensioned such that by way of pivoting the levers about their second articulation points the associated blade is movable from a first position which is close to the carrier element into at least one second position which is distanced further to the carrier element.

8. An intervertebral preparation tool according to claim 1, wherein the first and the second levers are articulated such that for moving the connected blade the first and the second levers both pivot in the same direction.

9. An intervertebral preparation tool according to claim 1, wherein the third lever is articulated such that for moving the connected blade the third lever pivots in a rotation direction which is opposite to the rotation direction of the first and/or the second lever given their simultaneous pivoting.

10. An intervertebral preparation tool according to claim 1, wherein the first lever and the second lever which are articulated on the blade have the same length between their first and second articulation points.

11. An intervertebral preparation tool according to claim 1, wherein the second lever and the third lever which are articulated on the blade have the same length between their first and second articulation points.

12. An intervertebral preparation tool according to claim 1, wherein the first lever and the second lever which are articulated on the blade have different lengths between their first and second articulation points.

13. An intervertebral preparation tool according to claim 1, wherein the second lever and the third lever which are articulated on the blade have different lengths between their first and second articulation points.

14. An intervertebral preparation tool according to claim 1, further comprising an instrument shank wherein the cutting head is situated at a distal end of the instrument shank and the actuation rod is displaceably guided in the longitudinal direction of the instrument shank on or in the instrument shank.

15. An intervertebral preparation tool according to claim 1, wherein the second articulation points of the three levers which are articulated on the blade lie on a straight line which preferably extends parallel to a displacement direction of the actuation rod.

16. An intervertebral preparation tool according to claim 1, wherein the first articulation points of the three levers which are articulated on the blade lie on a straight line which extends parallel or at an angle to a displacement direction of the actuation rod.

17. An intervertebral preparation tool according to claim 1, wherein at least an outer side of the blade in at least one position extends at an angle to a longitudinal axis of the cutting head.

18. An intervertebral preparation tool according to claim 14, wherein the cutting head is arranged at the distal end of the instrument shank and a handle is arranged at the proximal end of the instrument shank, said handle comprising an actuation device which is coupled to the actuation rod for displacement thereof.

19. An intervertebral preparation tool according to claim 1, wherein at least a portion of the articulation rod is located at a position radially inward of the carrier element with respect to a longitudinal axis of the carrier element.

20. An intervertebral preparation tool according to claim 1, wherein the first lever comprises a first lever end portion and the second lever comprises a second lever end portion, each of the first lever end portion and the second lever end portion being located adjacent to a portion of the carrier element.

* * * * *